United States Patent [19]

Johnson et al.

[11] Patent Number: 4,618,584
[45] Date of Patent: Oct. 21, 1986

[54] ULTRAFILTRATION PURIFICATION OF GLUCOSE ISOMERASE

[75] Inventors: Richard A. Johnson; Richard L. Antrim, both of Clinton, Iowa; Norman E. Lloyd, Ridgefield, Conn.

[73] Assignee: Nabisco Brands, Inc., Parsippany, N.J.

[21] Appl. No.: 684,205

[22] Filed: Dec. 20, 1984

[51] Int. Cl.[4] ............................................. C12N 9/92
[52] U.S. Cl. .................................. 435/234; 435/814; 210/651
[58] Field of Search ................ 435/234, 814; 210/651

[56] References Cited
U.S. PATENT DOCUMENTS 4,522,725  6/1985  Koyama et al. ................ 210/651 X

FOREIGN PATENT DOCUMENTS 1004614  2/1977  Canada ................................ 435/234

OTHER PUBLICATIONS

Method in Enzymology, vol. 22, pp. 39–49 (1971).

*Primary Examiner*—Lionel M. Shapiro
*Attorney, Agent, or Firm*—Richard Kornutik

[57] ABSTRACT

This invention relates to a process for the production of a purified glucose isomerase enzyme which comprises contacting an enzyme extract containing glucose isomerase and impurities with a first polysulfone membrane not normally permeable to glucose isomerase, in the presence of a salt concentration capable of selectively inducing permeation of glucose isomerase through the membrane, and obtaining a glucose isomerase containing permeate.

20 Claims, 1 Drawing Figure

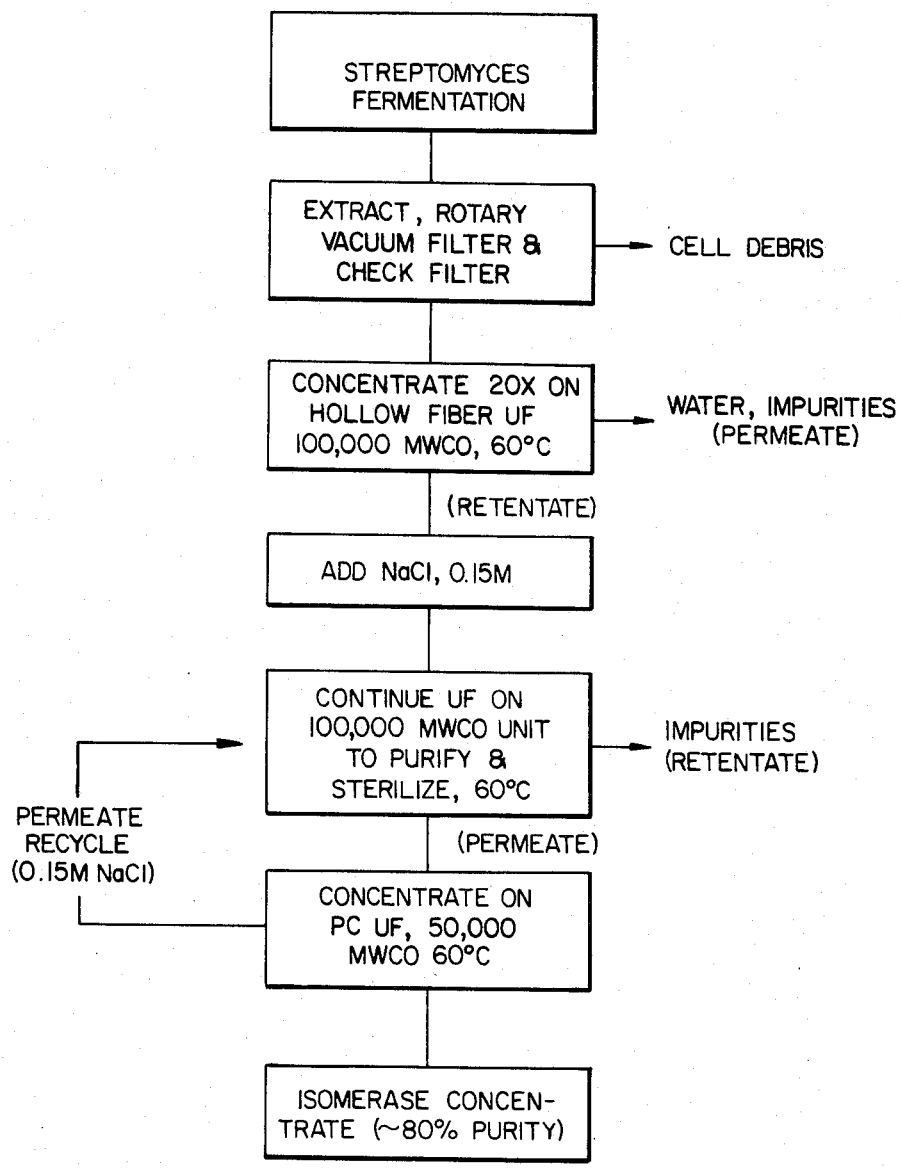
FIG. I

ULTRAFILTRATION PURIFICATION OF GLUCOSE ISOMERASE

FIELD OF THE INVENTION

The present invention relates to a process for enzyme purification. More specifically, the invention relates to a method for purification of glucose isomerase.

BACKGROUND OF THE INVENTION

The use of enzyme extracts from microorganisms in industry is widespread and profitable. Among the more common enzymes produced in a larger scale are bacterial proteases for use in making detergent powders, gluose oxidase for food preservation, and glucanases in the brewing industry. Many enzymes isolated for industrial use are extracellular, i.e., excreted into the growth medium by the microorganisms; isolation of such enzymes is usually a relatively simple matter. However, as is the case with, for example, glucose oxidase, many enzymes are produced intracellularly; extraction of the enzyme and removal of contaminants such as cellular debris and unwanted proteins presents an additional difficulty to the larger scale use of such products.

One particularly valuable intracellularly produced enzyme is glucose isomerase. This enzyme is produced by a wide variety of microorganisms, and is used to enzymatically catalyze the conversion of glucose, a relatively unsweet but inexpensive sugar to the sweeter sugar fructose. Examples of known procedures for this conversion may be found in Hamilton, et al. ("Glucose Isomerase, a Case Study of Enzyme-Catalyzed Process Technology" Immobilized Enzymes in Food and Microbial Processes, Olson, et al., Plenum Press, New York, (1974). pp. 94–106, 112, 115–137); and a number of other publications (Antrim, et al. "Glucose Isomerase Production of High-Fructose Syrups", *Applied Biochemistry and Bioengineering*, Vol. 2, Academic Press (1979); Chen, et al., "Glucose Isomerase (a review)", *Process Biochem.*, (1980) 15(6), pp. 36–41; Thompson, et al. "Fructose Manufacture from Glucose by Immobilized Glucose Isomerase", *Chem. Abstracts*, Vol. 82, (1975), Abs. No. 110316h; and Takasaki, "Fructose Production by Glucose Isomerase", *Chem. Abstracts*, Vol. 81, (1974), Abs. No. 7647a)

Although the enzyme is water soluble, performing the reaction in an aqueous solution presents the difficulty and expense of recovering the enzyme; a single use of the enzyme may also be rather costly. There are therefore a number of techniques for isomerization which involve immobilizing the enzyme so that substantial activity is retained while the enzyme is fixed to a water insoluble matrix. This arrangement allows for the repeated use of the enzymes for prolonged periods of time and with a number of different glucose containing solutions.

For such a system to function at maximum efficiency the immobilized enzyme should preferably be as pure as possible. This allows not only maximum loading, but also provides maximum specificity during conversion by ensuring a homogeneous enzyme product. A number of types of purification methods now exist. U.S. Pat. No. 4,007,842 describes a method in which a water insoluble organic solvent is added to an aqueous solution of this enzyme, causing precipitation of non-enzyme material, followed by treating the remaining solution with a soluble magnesium salt, which then causes the precipitation of an enzyme-magnesium complex. While effective, the method described therein is timeconsuming and relatively expensive. U.S. Pat. No. 4,250,263 describes a system in which a crude glucose-isomerase composition is heat-treated to precipitate non-enzyme material, leaving a glucose isomerase containing solution. Although this method is somewhat simpler than that noted above, the relative purity of the heat-treated solution is not very high. U.S. Pat. No. 4,256,838 discloses a method in which glucose isomerase is purified by treating an enzyme containing solution with a reagent which will precipitate nucleic acids, followed by chromatographing the remaining solution on a cellulose column, and eluting the enzyme. This method is not only rather complicated, but also provides a resulting enzyme solution with a yield of only about 70% of the original enzyme activity.

The present invention teaches a method of glucose isomerase purification which provides a final enzyme containing solution of unexpectedly high yield and purity, utilizing a technique heretofore unknown for glucose isomerase purification. It involves a process of ultrafiltration of an enzyme extract in combination with a selective elution of the enzyme by use of a salt solution. The salt treatment of the enzyme retained on a membrane has the surprising effect of inducing permeation of the enzyme through the membrane which would not otherwise allow its passage; the mechanism by which this unexpected result is obtained is unknown. The resulting enzyme solution contains a yield of at least 75–80% of the original crude enzyme extract activity, and which is least 80% pure enzyme. Such a product is particularly well suited for immobilization on an appropriate support.

BRIEF DESCRIPTION OF THE INVENTION

The present invention relates to a process for the production of a purified glucose isomerase enzyme which comprises contacting an enzyme extract containing glucose isomerase and impurities with a first membrane not normally permeable to glucose isomerase, in the presence of a salt concentration capable of selectively inducing permeation of glucose isomerase through the membrane, and obtaining a glucose isomerase-containing permeate. In a preferred embodiment, the enzyme-containing permeate is contacted with a second membrane of lower molecular weight cut-off to provide a purified enzyme concentrate. In a further embodiment, the permeate from the concentration step is recycled through a diafiltration reservoir for the salt induced permeation step, conserving both salt and water.

DETAILED DESCRIPTION OF THE FIGURE

FIG. 1 illustrates a block-flow diagram of the process for glucose isomerase purification.

DETAILED DESCRIPTION OF THE INVENTION

The process of the present invention provides an enzyme of sufficient yield and purity for further use in immobilization systems. The process described herein is equally useful and efficient in both a small-scale laboratory procedure as well as in a large-scale industrial application. In connection with the present process, it has been unexpectedly discovered that permeation of an enzyme which has been retained on an ultrafiltration membrane may be induced by the addition of salt to the retenate. The addition of the salt then allows the passage of a substantially purified enzyme through as a permeate, while most of the impurities remain bound to the membrane. The term ultrafiltration as used herein is defined as pressure driven filtration on a molecular scale; the process of diafiltration is also intended to be encompassed by this term.

In the present invention, the preferred salt to be used is NaCl. However, a number of other salts may also be used to produce the desired permeation. Among the alternative salts are $K_2SO_4$, $Na_2SO_4$, KCl, $NH_4$, Cl, $(NH_4)_2SO_4$, magnesium, manganese or cobalt salts, pyridinium chloride, and various nitrates, acetates, citrates and maleates. The latter groups, however, are subject to use under restricted conditions of pH. It is also possible, but not particularly practical, to utilize cationic or anionic polymers. Specifically not recommended are heavy metal or transition metal salts. It is a relatively simple matter, however, to determine the suitability of any particular salt by following the procedure described herein utilizing the salt of interest. Similarly, it is also possible to determine the optimum concentration of any of the Osalts by conducting trials similar to those described in Example 2.

The membrane will be one with a molecular weight cut-off (MWCO) below the molecular weight of the enzyme. In a preferred embodiment of this invention, the MWCO of the membrane is about 100,000; this is sufficient to retain a large proportion of the larger molecular weight impurities, especially viable microorganisms, as a retentate on the membrane, while the salt allows the enzyme to pass through in the permeate. It is also preferred that the membrane be of the polysulfone type, such as, Millipore PTAK polysulfide membrane or the Amicon HP 100-20 cartridge used in the Amicon CH4 concentrator. In present experience membranes of the cellulose or vinyl-acrylic type apparently do not provide the desired results under the conditions described herein.

The appropriate concentration of the necessary salt is dependent upon the purity of the starting composition. Significant enzyme permeation will occur at concentrations of 0.1–1.0 M NaCl and more; however, at concentrations of 1M NaCl, the flux across the membrane will be considerably reduced. When a crude enzyme extract is the starting material, the optimum NaCl concentration for enzyme permeation is about 0.5M. Although use of such an extract is feasible (Example 1), the yield of enzyme is generally fairly low, as is the purity of the resulting permeate. It is thus preferred to use a starting extract which has been partially purified and concentrated prior to the ultrafiltration in the presence of salt. The most preferred method of initial purification is by ultrafiltration in the presence of low salt concentration. Ultrafiltration with a 100,000 MWCO membrane will initially remove any lower molecular weight impurities, and serves to concentrate the enzyme about twentyfold; it consequently provides a starting material which, in the principle ultra-filtration step, will produce a permeate of relatively high purity. When such a partially purified, concentrated extract is used, it is possible to achieve enzyme permeation with concentrations of NaCl between about 0.1–0.3M. The preferred concentration in this circumstance is about 0.15–0.2M NaCl. When purification is performed prior to the principle ultrafiltration, the addition of the salt may be accomplished by direct addition of the appropriate amount of solid NaCl to the retentate, or by dilution of the retentate with a salt solution to provide the desired concentration of NaCl.

In the case in which a crude extract is used, the NaCl is added directly to the extract itself to provide the optimum level prior to ultrafiltration. The pH of the salt-containing solution is generally maintained within the range of 6–8, but is most preferably maintained around 7. During the salt induced permeation, the retentate may be diafiltered at constant volume with a salt solution of the required concentration, to replace the permeate being removed from the system.

Following the ultrafiltration-permeation step, the combined enzyme containing permeates may be concentrated and desalted by further ultrafiltration. This step is preferably achieved using a membrane of smaller MWCO than that used in previous ultrafiltrations. The permeate of this step may be recycled through the salt-solution diafiltration step. The preferred membrane for concentration is one with a MWCO of about 50,000. The final concentrated enzyme achieves a purity of at least 80% or more, and a recovery of enzyme activity of at least 75%.

An optional, but often useful, feature of the present invention is that, starting with the salt permeation step, all stages of the process may be carried out at elevated temperatures. There are a number of advantages of this practice. The first is that higher temperatures may reduce the chances of microbial contamination during any of the steps of the process. It may also serve to reduce the level of salt concentration required to induce permeation. Further, particularly at the salt permeation step, high temperatures may serve to denature unwanted proteins while not affecting the glucose isomerase. Generally speaking, temperatures of 50°–60° C. are sufficient to accomplish the above objectives. If the permeate of the salt-permeation step is heated as outlined above, however, it is desirable to filter the heat-treated solution to clarify it by removal of any denatured proteins. A general summary of the steps of the subject process is presented in FIG. 1.

Methods to produce the glucose isomerase extracts used as starting materials in the process of the present invention are well known in the art. For example, an enzyme extract containing glucose isomerase may be obtained by fermentation of microorganisms of a species known to produce glucose isomerase, extracting the enzyme from the mycelia and removing insoluble material by known methods.

The subject process may be used to purify glucose isomerase produced by any of the known glucose isomerase producers. Among the preferred organisms are those belonging to the genera Streptomyces, Aerobacter, Brevibacterium, Leuconostoc, Paracolobacterium, Nocardia, Micromonospora, Microbiospora and Arthrobacter. Also of interest are the glucose isomerases which are usually thermostable. Such enzymes will be less likely to be affected by the heat-treatment step. Organisms producing such heat-stable enzymes are *Bacillus stearothermophilus*, Ampulariella, and Pseudonocardia. The process of the present invention may be better understood by reference to the following non-limiting examples.

EXAMPLE 1

The following example describes the purification by salt-induced ultrafiltration/diafiltration of a crude enzyme extract, having a purity expressed in terms of specific activity of about 5 IGIU/mg protein.

An extract containing about 30 IGIU/ml suitable for this purpose can be prepared according to the teachings in Example 1 of U.S. Pat. No. 3,788,945. The IGIU unit of enzyme activity is defined, and an assay method described in "Automated Method for the Determination of D-Glucose Isomerase", N.E. Lloyd, et al.; *Cereal Chemistry*, 49(5) 544–553, September–October., 1972. Protein concentration is determined by measuring U.V. absorbance at 280 nm and equating 1.0 absorbance unit to a concentration of 1.0 mg/ml.

To determine the optimum conditions for isomerase permeation, portions of extract were used to prepare a series of solutions with salt concentrations (NaCl) ranging from 0.1 to 1.0 N. The conductivity and isomerase activity of each of these solutions was measured and 1000 ml portions were used for ultrafiltration under a standard set of conditions using an Amicon Model CH 4 concentrator (Amicon Corporation) with a 100,000 MWCO (HP 100-20) cartridge. Ultrafiltration time was recorded and aliquots of the permeate and retentate were taken for analyses.

The extract used for this study had a conductivity of 12,300 $\mu$mhos which corresponds to about 0.1 M NaCl. In all cases where salt was added at least 10% of the activity passed through the membrane and was collected in the permeate (Table I). Little activity, 0.4 IGIU/ml or 1.6% of the starting activity, permeated where no salt was added. The greatest permeation, 7.1 IGIU/ml or 16.4%, was achieved with 0.5 M NaCl addition. Increasing salt concentration up to 0.5 M NaCl increased enzyme permeation, but decreased flux. At 0.5 M NaCl the flux was 20 ml/min. for the cartridge which had a membrane surface area of 550 cm$^2$, or 400 ml $\times$ min$^{-1}$ $\times$ M$^{-1}$.

Results described above indicated that at the optimum salt concentration, 0.5 M, for enzyme permeation from crude extract, about 16% of the isomerase activity was found in the permeate from a single pass, i.e., 900 ml of permeate from 1000 ml starting extract. The flux at this salt concentration was 20.0 ml/min. To determine if most of the isomerase activity in the crude extract could be collected in the permeate from repeated diafiltration, a diafiltration series was carried out.

A portion of the extract was adjusted to pH 7.0, and sodium chloride was added (0.5 M). A 1000 ml portion of this solution was ultrafiltered as described previously until 900 ml of permeate had been collected. The permeate and retentate were sampled for analysis, and 900 ml of fresh 0.5 M NaCl was added to the retentate before ultrafiltration was resumed until 900 ml of retentate was collected. This sequence, i.e., ultrafiltration, dilution of the retentate, ultrafiltration, was repeated three more times. In each step the pressure drop across the system was maintained at 7 psig, and the average flux was determined by measuring the time to collect 900 ml of permeate.

The results are summarized in Table III. In the original ultrafiltration plus four diafiltrations a total of 26,825 IGIU or 65.4% of the starting activity was collected in the permeates. Both the flux and the per cent activity permeating (based on the starting activity for each step) increased with each successive step, probably as a result of decreasing concentration of permeable solids in the retentates. The flux during the fourth diafiltration was 39 ml/min. or almost double the flux for the first step ultrafiltration.

The permeates from all five steps were combined and ultrafiltered with a 50,000 MWCO cartridge using the CH4 concentrator. The retentate from this step was diafiltered twice with 5 volumes of deionized water. The resulting retentate contained a total of 26,230 IGIU with a specific activity of 17.2 IGIU/mg. This represents greater than a threefold increase in purity.

EXAMPLE 2

The following example illustrates the procedure using an enzyme extract which has been partially purified.

A significant portion of the lower molecular weight impurities present in crude isomerase extracts can be removed by simple ultrafiltration-concentration with a 100,000 MWCO membrane at low salt concentration. In this case, the enzyme is almost quantitatively retained by the membrane while impurities are removed with the permeate To test the effectiveness of salt-induced permeation on such a preparation, a portion of extract as in Example 1 was first concentrated ~20 fold by ultrafiltration with an Amicon CH4 concentrator using the 100,000 MWCO cartridge. The concentrate was then diluted to 41 IGIU/ml with water and the pH was adjusted to 7.0 before the addition of various amounts of NaCl to prepare a series of enzyme solutions ranging from 0.1 to 1.0 M salt. A 1000 ml portion of each solution was then ultrafiltered with the CH$_4$ concentrator as described above. The results are shown in Table II.

In all trials where sodium chloride was added at least 13% of the activity passed through the membrane. Increasing salt concentration from 0.2 M to 0.5 M resulted in decreasing isomerase permeation, while at 1.0 M NaCl, 31.1% of the activity permeated. In all cases, enzyme permeation was significantly greater than from the crude extract (Table I) at similar enzyme and salt concentration. This latter observation probably reflects the removal by prior ultrafiltration of impurities which would otherwise compete with isomerase for permeation through the membrane pores. A trial with MgSO$_4$ addition (0.16 M) was included to demonstrate that the salt of a divalent cation and anion would be as effective as sodium chloride in promoting enzyme permeation.

Flux decreased with increasing salt concentration, probably due to a competition effect between salt and enzyme for membrane pores. Thus, the optimum salt concentration for both enzyme permeation and flux appears to be 0.2 M.

To determine the rate and extent of isomerase permeation from an ultrafiltered concentrate, a 40-fold ultrafiltered concentrate (100,000 MWCO) of extract was prepared. A portion of the concentrate was diluted to ~41 IGIU/ml with 0.2 M NaCl and a 1000 ml aliquot was ultrafiltered with the 100,000 MWCO as described in previous experiments. After collecting 900 ml of permeate, samples of both the permeate and retentate were taken for analyses, and the retentate was diluted with 900 ml of fresh 0.2 M NaCl. Ultrafiltration was then resumed until 900 ml of permeate had been collected.

The retentate was then diluted with 100 ml of 0.2 NaCl (total volume–200 ml) and a constant volume diafiltration was run, as illustrated in FIG. 1, by continuous addition of 0.2 M NaCl to replace permeate which was removed from the system. A total of 2000 ml of permeate was collected in fractions to monitor the progress of the diafiltration. Flux was monitored by measuring the time to collect each fraction, and samples of each fraction were analyzed for isomerase activity.

A total of 30,950 IGIU or 75.5% of the starting activity was collected in the permeates from ultrafiltration, diafiltration, and constant volume diafiltration. The initial flux for the ultrafiltration was 41 ml/min. The flux increased constantly over the course of the constant volume diafiltration to a final value of 52 ml/min.

The combined permeates were concentrated and desalted by ultrafiltration-diafiltration with a 50,000 MWCO cartridge. The concentrated enzyme, 30,980 IGIU total, had a specific activity of 34.4 IGIU/mg, which represents a 7-fold increase in purity.

EXAMPLE 3

The following example illustrates the permeation-diafiltration procedure utilizing an undiluted concentrate.

To reduce the volume of salt solution needed for diafiltration the procedure of Example 2 was repeated with several modifications. In this case, an enzyme concentrate prepared by 100,000 MWCO ultrafiltration was used directly after the addition of solid sodium chloride to a final concentration of 0.2 M. A 200 ml portion of this concentrate (432 IGIU/ml) was diafiltered at constant volume with 0.2 M NaCl, and the permeate was collected in 100 ml fractions. After collecting 1200 ml of permeate the retentate volume was reduced to −100 ml by temporarily interrupting the influx of 0.2 M NaCl. Diafiltration was then continued at a constant retentate volume of ~100 ml. Permeate fractions were analyzed for isomerase activity and protein concentration (U.V.).

During diafiltration the permeate activity (IGIU/ml) decreased gradually, and the flux increased to a high of 38.5 ml/min. When the retentate volume was reduced to 100 ml after 1200 ml of permeate had been collected, the permeate activity increased temporarily, and the flux dropped to about 33 ml/min.

A total of 46,582 IGIU or 54% of the starting activity was collected in 2000 ml of permeate for an average potency of 23.5 IGIU/ml. The specific activity of the permeate ranged from 31.9 to 38.3 IGIU/mg with an average of 35.1 IGIU/mg.

EXAMPLE 4

The following example illustrates a step-by-step complete procedure, including a heat-treatment step, as performed on a relatively larger scale:

A. Concentration and Partial Purification of Crude Extract

A 25-liter batch of isomerase extract as in Example 1 was clarified by filtration through a precoat of filteraid followed by filtration through a Gelman 0.45μ minicapsule filter. After adjusting the pH to 7.0, the filtered extract at a potency of 38.0 IGIU/ml was ultrafiltered with an Amicon CH4 concentrator using an HP100-20 cartridge (100,000 MWCO). Ultrafiltration was carried out at room temperature, 7 psig pressure drop, until the permeate volume was reduced to ~1200 ml. The retentate was then diluted with 6000 ml of deionized water, and ultrafiltration (diafiltration) was resumed. Diafiltration increased the final purity by about 5% and could be considered as an option in a scaled-up process. The retentate from this diafiltration step contained a total of 896,000 IGIU at a potency of 854 IGIU/ml. Total volume was 1.8 liters.

Thus the recovery, based on the total starting activity in the extract (950,000 IGIU) was 94.3%.

B. Salt-Induced Enzyme Permeation Via Constant Volume

Diafiltration at 60° C.

A 500 ml portion of the concentrated enzyme was adjusted to a conductivity of 15,000 μmhos (~0.15 M) by the addition of solid NaCl after adding MgSO$_4$ (1 mM) and MnCl$_2$ (0.2 mM). This solution was heated to ~62° C. and held for 20 minutes.

The purpose of the heat step was to precipitate a small amount of protein which might otherwise precipitate during further 60° C. operations. It may be optional in a scaled-up version. The purpose for operating at 60° C. was to increase flux by 4 or 5 fold over the low temperature alternative of about 15° C., and to prevent microbial contamination.

The slight haze which formed during the heat treatment was removed by filtration through a 0.45 μ microfilter. The clarified filtrate contained a total of 422,000 IGIU at a potency of 824 IGIU/ml for a recovery of 98.8% of the activity across the heat treatment step.

A 250 ml portion of the heat-treated enzyme was used for constant-volume diafiltration at 60° C. using an Amicon CH4 concentrator with a HP100-20 cartridge (100,000 MWCO). A total of 4000 ml of 0.15 N NaCl (15,000 μmhos conductivity) was used for the initial stages of diafiltration. The permeate from diafiltration was collected in 1000 ml fractions. Flux was estimated by measuring the time to collect each 1000 ml fraction. After sampling for analysis, the permeate fractions were ultrafiltered with a CH4 concentrator using an H1X50-20 cartridge. Flux for the 50,000 MWCO ultrafiltration was measured in the usual manner and periodic samples of the permeate were taken for analyses.

The 50,000 MWCO permeate, which contained less than 0.6 IGIU/ml isomerase activity, was used to supply the diafiltration reservoir for the salt-induced permeation step after the initial 4000 ml of salt solution had been used.

The following table shows the results of the salt-induced permeation for the initial 250 ml of enzyme concentrate.

| Fraction | Flux ml/min | Permeate Activity | | |
|---|---|---|---|---|
| | | IGIU/ml | IGIU/1000 ml | IGIU Total |
| 1 | 23.8 | 80.3 | 80,300 | 80,300 |
| 2 | 22.2 | 36.3 | 36,300 | 116,600 |
| 3 | 22.7 | 18.2 | 18,200 | 134,800 |
| 4 | 23.4 | 11.5 | 11,500 | 146,300 |
| 5* | 23.4 | 10.0 | 10,000 | 156,300 |
| 6* | 21.4 | 9.7 | 9,700 | 166,000 |

*Diafiltered with 50,000 MWCO Permeate

A total of 166,000 IGIU was accumulated in the 6000 ml of permeate for an average potency of 27.7 IGIU/ml and a recovery of 80.6% of the starting activity. The average flux was about 23 ml/min.

Near the end of diafiltration the retentate volume was reduced to ~100 ml by interrupting the flow of salt solution. The retentate was centrifuged to remove the insoluble haze, and the clear supernate was assayed for residual isomerase activity. The clarified retentate contained a total of 26,300 IGIU. Thus, the total recovery in the permeate plus retentate was 192,300 IGIU or 95.3% of the starting activity.

The clarified retentate was returned to the constant volume diafiltration, and 200 ml of fresh enzyme concentrate (164,800 IGIU) was added. The constant-volume diafiltration was then resumed using the 50,000 MWCO permeate as diafiltration medium. Fractions were collected and assayed as usual. After collecting 3000 ml of permeate an additional 50 ml of fresh enzyme solution (41,200 IGIU) was added to the retentate and diafiltration was continued. The results are summarized in the following table.

| Fraction | Flux ml/min | Permeate Activity | | |
|---|---|---|---|---|
| | | IGIU/ml | IGIU/1000 ml | IGIU Total |
| 1 | 25.6 | 86.1 | 86,100 | 86,100 |
| 2 | 26.7 | 40.5 | 40,500 | 126,600 |
| 3 | 26.9 | 20.2 | 20,200 | 146,800 |
| 4 | 25.2 | 26.0 | 26,000 | 172,800 |
| 5 | 24.8 | 16.9 | 16,900 | 189,700 |

A total of 189,700 IGIU was collected in the permeate. This represented 81.7% of the starting activity with an average potency of 34.9 IGIU/ml permeate. The final retentate contained a total of 33,200 IGIU so that the overall recovery in the permeate plus retentate was 222,900 IGIU or 95.9%.

Some insoluble material also formed during this second diafiltration. However, this did not appear to be a serious problem since the average flux was about 26 ml/min.

In the two diafiltrations described above a total of 500 ml of enzyme concentrate of 412,000 IGIU was processed using only 4000 ml of ~0.15 M NaCl solution. A total of about 7000 ml of 50,000 MWCO permeate was recycled to the salt permeation step. A total of 11,000 ml of 100,000 MWCO permeate containing 355,700 IGIU or 86.3% of starting activity was collected and concentrated by 50,000 MWCO ultrafiltration.

C. Permeate Concentration By 50,000 MWCO Ultrafiltration

The entire permeate from the 100,000 MWCO ultrafiltration was ultrafiltered with a 50,000 MWCO cartridge to concentrate the enzyme. Each 1000 ml fraction of 100,000 MWCO permeate, after sampling for analyses, was added directly to the 50,000 MWCO step.

The permeate from the 50,000 MWCO ultrafiltration was collected in 1000 ml fractions, sampled for analyses, and recycled to the 100,000 MWCO permeation step. The flux across the 50,000 MWCO step ranged from a starting high of ~9 ml/min (550 cm$^3$ membrane area) to a final rate of 5.1 ml/min. during the final stages of concentration. No isomerase activity (<0.6 IGIU/ml) was found in the 50,000 MWCO permeate.

The 50,000 ml retentate was reduced to a final volume of 295 ml. The total isomerase activity in this concentrate was 336,300 IGIU (1140 IGIU/ml). This was 94.7% of the activity in the 100,000 MWCO permeate. The specific activity of the concentrated enzyme was 35.7 IGIU/mg, which represents a 7 fold increase in purity.

If desired, the final concentrate could be concentrated further by ultrafiltration to prepare a potent stable concentrate. The concentrate could also be diafiltered to remove residual sodium chloride.

FIG. 1 summarizes the process in block-flow form.

TABLE I
THE EFFECT OF SODIUM CHLORIDE CONCENTRATION ON ISOMERASE PERMEATION FROM CRUDE ENZYME EXTRACT

| [NaCl] M | Conductivity mhos | Flux* ml/min | Permeate Activity | | % Permeated** |
|---|---|---|---|---|---|
| | | | IGIU/ml | IGIU Total | |
| 0 | 12.3 | 30.0 | 0.4 | 642 | 1.6 |
| 0.1 | 19.7 | 26.5 | 4.6 | 4231 | 10.3 |
| 0.2 | 30.2 | 24.3 | 5.0 | 4650 | 11.3 |
| 0.3 | 37.8 | 21.4 | 5.2 | 4790 | 11.6 |
| 0.4 | 45.4 | 19.6 | 5.8 | 5365 | 13.0 |
| 0.5 | 52.2 | 20.0 | 7.1 | 6745 | 16.4 |
| 1.0 | 84.2 | 19.6 | 5.3 | 5016 | 12.2 |

TABLE II
THE EFFECT OF SALT CONCENTRATION ON ISOMERASE PERMEATION FROM ULTRAFILTERED ENZYME

| [NaCl] M | Conductivity mhos | Flux* ml/min | Permeate Activity | | % Permeated |
|---|---|---|---|---|---|
| | | | IGIU/ml | IGIU Total | |
| 0 | 0.7 | 42.9 | 0.17 | 158 | 0.4 |
| 0.1 | 9.8 | 42.9 | 8.2 | 7564 | 18.4 |
| 0.2 | 19.8 | 40.9 | 8.9 | 8259 | 20.0 |
| 0.3 | 29.2 | 36.0 | 8.1 | 7415 | 19.0 |
| 0.4 | 37.2 | 39.1 | 6.6 | 6101 | 14.8 |
| 0.5 | 45.0 | 34.6 | 6.0 | 5520 | 13.4 |
| 1.0 | 79.7 | 32.1 | 13.6 | 12822 | 31.1 |
| 0.16 MgSO$_4$ | 13.3 | 25.7 | 5.4 | 4923 | 11.9 |

*Avg. Flow Rate Determined By Measuring Time To Collect 900 ml Permeate
**Total Activity In 900 ml Permeate/41,000 IGIU Starting Activity

TABLE III
ULTRAFILTRATION-DIAFILTRATION OF CRUDE ENZYME EXTRACT

| Step | Flux ml/min | Permeate Activity | | Retentate Act. IGIU Total | % Permeated* |
|---|---|---|---|---|---|
| | | IGIU/ml | IGIU Total | | |
| Ultrafiltration | 20 | 7.1 | 6745 | 33,400 | 16.5 |
| Diafiltration 1 | 23 | 5.9 | 5355 | 27,400 | 16.0 |
| Diafiltration 2 | 27 | 5.7 | 5130 | 18,800 | 18.7 |
| Diafiltration 3 | 32 | 4.8 | 4320 | 13,470 | 23.0 |
| Diafiltration 4 | 39 | 5.5 | 5115 | 7,066 | 38.0 |

*Based On Retentate Activity At The Start Of Each Step

What is claimed is:

1. A process for the production of a purified glucose isomerase enzyme which comprises contacting an enzyme extract containing glucose isomerase and impurities with a first polysulfone membrane not normally permeable to glucose isomerase, in the presence of a salt concentration capable of selectively inducing permeation of glucose isomerase through the membrane, and obtaining a glucose isomerase containing permeate.

2. The process of claim 1 wherein the salt is NaCl, KCl, Na$_2$SO$_4$, K$_2$SO$_4$, NH$_4$Cl, (NH$_4$)$_2$SO$_4$, magnesium, manganese or cobalt salts, pyridinium chloride, or nitrate, citrate, acetate or maleate salts.

3. The process of claim 1 wherein the salt is NaCl.

4. The process of claim 1 which comprises the further step of concentrating the permeate by contacting it with a second membrane not normally permeable to glucose isomerase, and having a lower molecular weight cut-off than the first membrane.

5. The process of claim 3 wherein the enzyme extract has been previously partially purified.

6. The process of claim 5 wherein the enzyme extract has been previously partially purified by contacting the extract with a membrane not normally permeable to glucose isomerase.

7. The process of claim 3 wherein the salt concentration is about 0.1–1.0M NaCl.

8. The process of claim 5 wherein the salt concentration is about 0.1–0.3M NaCl.

9. The process of claim 1 wherein the membrane has a molecular weight cut-off of about 100,000.

10. The process of claim 4 wherein the membrane has a molecular weight cut-off of about 50,000.

11. The process of claim 6 wherein the membrane has a molecular weight cut off of about 100,000.

12. The process of claim 1 wherein the permeate is heated to a temperature of about 50°–65° C.

13. The process of claim 1 which comprises the further step of recovering the enzyme.

14. The process of claim 4 which comprises the further step of recovering the enzyme.

15. The process of claim 5 which comprises the further step of recovering the enzyme.

16. A process for the production of a purified glucose isomerase enzyme which comprises (a) partially purifying an enzyme extract containing glucose isomerase and impurities;

(b) contacting the extract with a first polysulfone membrane not normally permeable to glucose isomerase, in the presence of a salt concentration capable of inducing permeation of glucose isomerase through the membrane;

(c) obtaining a glucose isomerase-containing permeate;

(d) concentrating the glucose isomerase-containing permeate by contact with a second polysulfone membrane with a molecular weight cut-off below that of the first membrane and obtaining a glucose isomerase containing retentate and a second permeate;

(e) repeating the procedures of steps (b) and (c) using the second permeate as a diafiltration medium.

17. The process of claim 16 wherein the salt is NaCl.

18. The process of claim 16 wherein the salt concentration is about 0.1–0.3M NaCl.

19. The process of claim 16 wherein the first membrane has a molecular weight cut-off of about 100,000.

20. The process of claim 16 wherein the second membrane has a molecular weight cut-off of about 50,000.

* * * * *